(12) United States Patent
Kim (10) Patent No.: US 12,306,278 B2
(45) Date of Patent: May 20, 2025

(54) MAGNETIC RESONANCE IMAGE PROCESSING APPARATUS AND METHOD TO WHICH IMPROVEMENT IN SLICE RESOLUTION IS APPLIED

(71) Applicant: AIRS MEDICAL INC., Seoul (KR)

(72) Inventor: Jeewook Kim, Seoul (KR)

(73) Assignee: AIRS MEDICAL INC., Seoul (KR)

( * ) Notice: Subject to any disclaimer, the term of this patent is extended or adjusted under 35 U.S.C. 154(b) by 0 days.

(21) Appl. No.: 17/790,836

(22) PCT Filed: Apr. 7, 2022

(86) PCT No.: PCT/KR2022/005011
§ 371 (c)(1),
(2) Date: Jul. 5, 2022

(87) PCT Pub. No.: WO2022/216073
PCT Pub. Date: Oct. 13, 2022

(65) Prior Publication Data
US 2024/0159848 A1    May 16, 2024

(30) Foreign Application Priority Data
Apr. 8, 2021 (KR) .................. 10-2021-0045813

(51) Int. Cl.
*G01R 33/56* (2006.01)
*G06T 7/00* (2017.01)

(52) U.S. Cl.
CPC ........ *G01R 33/5608* (2013.01); *G06T 7/0012* (2013.01); *G06T 2207/10088* (2013.01);
(Continued)

(58) Field of Classification Search
CPC .. G01R 33/5608; G01R 33/56; G06T 7/0012; G06T 2207/10088; G06T 2207/20081;
(Continued)

(56) References Cited

U.S. PATENT DOCUMENTS

2010/0298719 A1*  11/2010  Kock ..................... G16Z 99/00
                                                                 600/485
2014/0219531 A1*   8/2014  Epstein .................... G06T 7/20
                                                                 382/131
(Continued)

FOREIGN PATENT DOCUMENTS

KR  10-2019-0038333 A   4/2019
WO  WO-2019/039708 A1   2/2019

OTHER PUBLICATIONS

Du, T., et al.; "Adaptive convolutional neural networks for κ-space data interpolation in fast magnetic resonance imaging", arXiv, 2020, p. 1-13.
(Continued)

*Primary Examiner* — Iriana Cruz
(74) *Attorney, Agent, or Firm* — Harness, Dickey & Pierce, P.L.C.

(57) ABSTRACT

According to an embodiment of the present invention, there is provided a magnetic resonance image processing method, the magnetic resonance image processing method being performed by a magnetic resonance image processing apparatus, the magnetic resonance image processing method including: inputting an input image having a slice resolution higher than 0 and lower than 1 to an artificial neural network model; and outputting an output image having a slice resolution of 1 from the artificial neural network model.

10 Claims, 6 Drawing Sheets

(52) U.S. Cl.
CPC ............ *G06T 2207/20081* (2013.01); *G06T 2207/20084* (2013.01)

(58) Field of Classification Search
CPC ............ G06T 2207/20084; G06T 7/00; A61B 5/7267; A61B 2576/00; A61B 5/055; A61B 5/0033; G06N 3/045; G06N 3/08; G06N 20/00; G16H 30/40; G16H 50/70
See application file for complete search history.

(56) References Cited

U.S. PATENT DOCUMENTS

| | | | |
|---|---|---|---|
| 2018/0315188 A1* | 11/2018 | Tegzes | ............... G06T 7/11 |
| 2019/0244399 A1 | 8/2019 | Li et al. | |
| 2022/0075017 A1* | 3/2022 | Sabuncu | ............ G01R 33/561 |
| 2022/0092739 A1* | 3/2022 | Li | ............ G06T 3/4046 |

OTHER PUBLICATIONS

Chaudhari, A. S., et al.; "Super-Resolution Musculoskeletal MRI Using Deep Learning", Magn Reson Med. Nov. 2018 ; 80(5):2139-2154.

* cited by examiner

MAGNETIC RESONANCE IMAGE PROCESSING APPARATUS AND METHOD TO WHICH IMPROVEMENT IN SLICE RESOLUTION IS APPLIED

CROSS-REFERENCE TO RELATED APPLICATION

This application is a national phase entry of PCT Application No. PCT/KR2022/005011, filed on 7 Apr. 2022 and claims priority to Korean Patent Application No. 10-2021-0045813, filed on 8 Apr. 2021. The entire disclosures of the applications identified in this paragraph are incorporated herein by references.

TECHNICAL FIELD

The present invention relates to a magnetic resonance image processing apparatus and method to which an improvement in slice resolution is applied, and more particularly to a magnetic resonance image processing apparatus and method that accelerate the acquisition of a magnetic resonance image from a magnetic resonance signal by using an artificial neural network.

BACKGROUND ART

In general, medical imaging machines are apparatuses that acquire information about the body of a patient and provide an image. Medical imaging machines include X-ray machines, ultrasound diagnostic scanners, computed tomography scanners, magnetic resonance imaging (MRI) machines, etc.

A magnetic resonance image is an image acquired by imaging the density and physical/chemical properties of atomic nuclei by generating nuclear magnetic resonance in the atomic nuclei nucleus of hydrogen in the human body using a magnetic field and non-ionizing radiation that are harmless to the human body. Magnetic resonance imaging machines occupy an important position in the field of diagnosis using medical images because the imaging conditions thereof are relatively free and they provide images including various types of diagnostic information from soft tissues and having desirable contrast.

Meanwhile, the imaging performed by such magnetic resonance imaging machines may take time ranging from about 20 minutes to about 1 hour depending on an imaging target region and the type of magnetic resonance image. In other words, a drawback arises in that the imaging time of the magnetic resonance imaging machines is longer than those of other types of medical imaging machines. This drawback may impose a burden regarding imaging on a patient. In particular, the drawback makes it difficult to apply magnetic resonance imaging to a patient with claustrophobia. Therefore, technologies for shortening imaging time have been developed until recently, and also, there is a demand for an improvement in image quality.

SUMMARY

Technical Problem

A magnetic resonance image processing apparatus and method according to embodiments of the present invention are intended to acquire a magnetic resonance image having a slice resolution of 1 by using an acceleratedly imaged magnetic resonance image having a slice resolution higher than 0 and lower than 1 and an artificial neural network model.

Furthermore, a magnetic resonance image processing apparatus and method according to embodiments of the present invention are intended to acquire a magnetic resonance image having an improved slice resolution and an improved resolution by using an artificial neural network model trained only on training image data having a low slice resolution when there is no training image data having a high slice resolution.

Technical Solution

According to an embodiment of the present invention, there is provided a magnetic resonance image processing method, the magnetic resonance image processing method being performed by a magnetic resonance image processing apparatus, the magnetic resonance image processing method including: inputting an input image having a slice resolution higher than 0 and lower than 1 to an artificial neural network model; and outputting an output image having a slice resolution of 1 from the artificial neural network model.

In the present invention, the artificial neural network model has been trained with training input data including image data having a slice resolution higher than 0 and lower than 1 and training label data including image data having a slice resolution of 1.

In the present invention, the training input data includes image data having a slice resolution higher than 0 and lower than 1 that is measured based on the setting of a slice resolution of the input image to 1, and the training label data includes image data having the same slice resolution as the input image.

In the present invention, the training input data includes a training image and a slice image adjacent to the training image, and a combination of the training image and the slice image adjacent to the training image is input to the artificial neural network model and the artificial neural network model is trained on the combination.

In the present invention, the input image includes a target image for which a slice resolution is to be increased and a slice image adjacent to the target image, and a combination of the target image and the slice image adjacent to the target image is input to the artificial neural network model.

In the present invention, the input image includes at least one of a k-space image and a DICOM image.

According to an embodiment of the present invention, there is provided a magnetic resonance image processing apparatus, wherein an input image having a slice resolution higher than 0 and lower than 1 is input to an artificial neural network model, and an output image having a slice resolution of 1 is output from the artificial neural network model.

In the present invention, the artificial neural network model has been trained with training input data including image data having a slice resolution higher than 0 and lower than 1 and training label data including image data having a slice resolution of 1.

In the present invention, the training input data includes image data having a slice resolution higher than 0 and lower than 1 that is measured based on the setting of a slice resolution of the input image to 1, and the training label data includes image data having the same slice resolution as the input image.

In the present invention, the training input data includes a training image and a slice image adjacent to the training image, and a combination of the training image and the slice image adjacent to the training image is input to the artificial neural network model and the artificial neural network model is trained on the combination.

In the present invention, the input image includes a target image for which a slice resolution is to be increased and a slice image adjacent to the target image, and a combination of the target image and the slice image adjacent to the target image is input to the artificial neural network model.

In the present invention, the input image includes at least one of a k-space image and a DICOM image.

Advantageous Effects

The magnetic resonance image processing apparatus and method according to the embodiments of the present invention may acquire a magnetic resonance image having a slice resolution of 1 by using an acceleratedly imaged magnetic resonance image having a slice resolution higher than 0 and lower than 1 and an artificial neural network model.

Furthermore, the magnetic resonance image processing apparatus and method according to the embodiments of the present invention may acquire a magnetic resonance image having an improved slice resolution and an improved resolution by using an artificial neural network model trained only on training image data having a low slice resolution when there is no training image data having a high slice resolution.

DETAILED DESCRIPTION

Embodiments of the present invention will be described in detail below with reference to the accompanying drawings so that those of ordinary skill in the art to which the present invention pertains may easily practice the present invention. However, the present invention may be implemented in various different forms, and is not limited to the embodiments described herein. Furthermore, in the drawings, portions not related to the description are omitted for the clear description of the present invention, and like reference numerals are assigned to like portions throughout the specification.

Throughout the specification, when a part is described as being connected to another part, this includes not only a case in which they are "directly connected" to each other but also a case in which they are "electrically connected" to each other with another element interposed therebetween. In addition, when a part is described as "including" a component, this means that the part may further include another component, rather than excluding another component, unless otherwise described.

In the present specification, the 'server' refers to a computer configured to include one or more pieces of memory, one or more computer processors, and one or more programs. In this case, one or more programs are configured to be stored in memory and to be executed by one or more processors. The one or more pieces of memory, the one or more computer processors, and the one or more programs may be located in the physically same apparatus, and may be directly connected to each other or be connected to each other over a communication network.

In the present specification, the 'image' may refer to multi-dimensional data composed of discrete image elements (e.g., pixels in a 2D image or voxels in a 3D image). For example, an image may include medical images acquired by medical imaging machines such as a magnetic resonance imaging (MRI) machine, a computed tomography (CT) scanner, an ultrasonic scanner, and an X-ray machine.

In the present specification, the 'image restoration' may include improving the resolution of an image having a low resolution or improving the quality of an image having a low quality. Furthermore, in the case of MRI, 'image restoration' may refer to processing an image generated from sub-sampled k-space data in the same manner as/in a manner similar to that of an image generated from fully sampled k-space data as well as the above-mentioned meaning.

A magnetic resonance image processing apparatus according to an embodiment of the present invention will be described in detail below with reference to the accompanying drawings.

Figure 1:
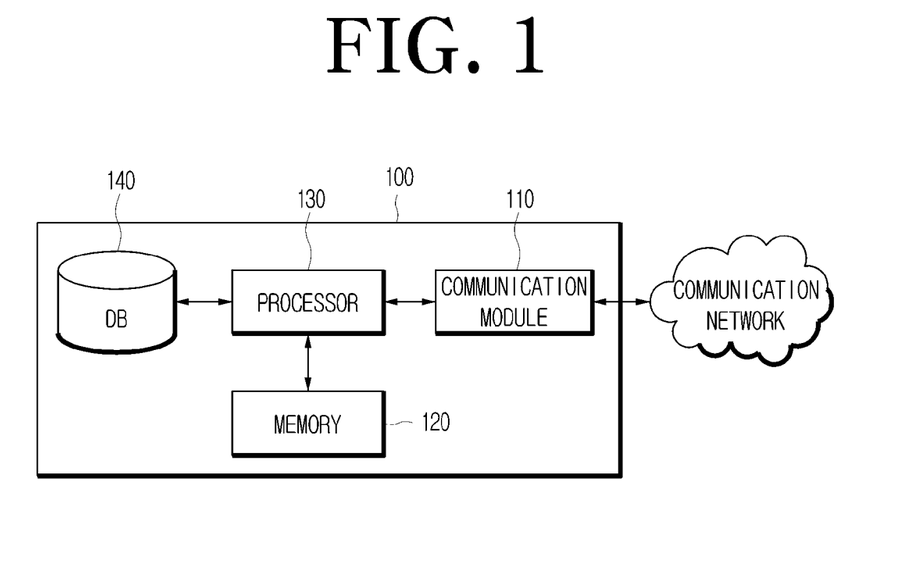
FIG. 1 is a diagram illustrating the configuration of a magnetic resonance image processing apparatus according to an embodiment of the present invention.

FIG. 1 is a diagram illustrating the configuration of a magnetic resonance image processing apparatus according to an embodiment of the present invention.

Referring to FIG. 1, a magnetic resonance image processing apparatus 100 may include not only an MRI system capable of acquiring a magnetic resonance image by detecting a magnetic resonance signal on its own, but also an image processing apparatus for processing an image acquired from the outside and a smartphone, a tablet personal computer (PC), a PC, a smart TV, a micro-server, a cloud server, other home appliances, and other mobile or non-mobile computing devices equipped with a function of processing a magnetic resonance image, but is not limited thereto. In addition, the magnetic resonance image processing apparatus 100 may be a wearable device, such as a watch, glasses, a hairband, or a ring, equipped with a communication function and a data processing function.

Furthermore, the magnetic resonance image processing apparatus 100 according to an embodiment of the present invention may be directed to a magnetic resonance image processing apparatus 100 that transmits and receives medical image data while communicating with a picture archiving and communication system (PACS) and/or a magnetic resonance imaging apparatus (not shown) used in a medical institution and reconstructs magnetic resonance image data by using an artificial neural network model.

More specifically, the magnetic resonance image processing apparatus 100 according to an embodiment of the present invention may be implemented in the form of a cloud computing system. Cloud computing is a computing environment in which IT-related services such as data storage, networking, and the use of content can be used in an integrated manner through a server on the Internet. Alternatively, the magnetic resonance image processing apparatus 100 may be implemented as various types of computing systems capable of performing a magnetic resonance image processing method such as server computing, edge computing, and serverless computing.

The magnetic resonance image processing apparatus 100 according to an embodiment of the present invention may include a communication module 110, memory 120, a processor 130, and a database 140.

The communication module 110 provides a communication interface to the magnetic resonance image processing apparatus while operating in conjunction with a communication network. The magnetic resonance image processing apparatus 100 may transmit and receive data to and from a client terminal, a PACS terminal, and a PACS server to be described later by using the communication module 110. In this case, the communication module 110 may be a device including hardware and software necessary to transmit and receive signals, such as control signals or data signals, to and from another network device over a wired/wireless connection.

Meanwhile, in the present invention, the 'terminal' may be a wireless communication device with guaranteed portability and mobility, and may be one of all types of handheld-based wireless communication devices such as a smartphone, a tablet PC, or a notebook. Furthermore, the 'terminal' may be a wearable device, such as a watch, glasses, a hairband or a ring, equipped with a communication function and a data processing function. Moreover, the 'terminal' may be a wired communication device, such as a PC, that can be connected to another terminal or a server over a network.

The memory 120 may be a storage medium in which a program executed in the magnetic resonance image processing apparatus 100 is recorded. Furthermore, the memory 120 may perform the function of temporarily or permanently storing data that is processed by the processor. In this case, although the memory 120 may include volatile storage media or nonvolatile storage media, the scope of the present invention is not limited thereto.

The processor 130 may control the overall process of the program that is executed in the magnetic resonance image processing apparatus 100. In this case, the processor 130 may include all types of devices capable of processing data, such as a processor. In this case, for example, the 'processor' may refer to a data processing device embedded in hardware, which has circuits physically structured to perform functions represented by codes or instructions included in a program. Although as an example of the data processing device embedded in hardware as described above, processing devices such as a microprocessor, a central processing unit (CPU), a processor core, a multiprocessor, an application-specific integrated circuit (ASIC), and a field-programmable gate array (FPGA), may be enumerated, the scope of the present invention is not limited thereto.

The database 140 may be a component in which various types of data necessary for the magnetic resonance image processing apparatus to execute a program are stored. For example, the database 140 may be a component in which a user list, a worklist, image processing information, protocol rules, medical image data, an artificial neural network model 400, and training data are stored.

Meanwhile, a client terminal configured to control an imaging device or manage the transmission of medical image data in conjunction with a medical imaging machine and a PACS terminal installed with a PACS program and configured to allow medical staff to view, process, and manage medical image data may be generally deployed in a medical institution.

The client terminal may be a terminal on which a program providing a user interface (UI) configured to output user login, a worklist, and image processing details is installed. The PACS terminal may be a terminal on which a program providing a user interface configured to transmit medical image data and personal information data, stored in the PACS server, to the magnetic resonance image processing apparatus 100 and to receive the medical image data reconstructed via the artificial neural network model 400 and then store it in the PACS server or output it to a display is installed.

A magnetic resonance image processing method using the magnetic resonance image processing apparatus 100 according to an embodiment of the present invention will be described in detail below.

Figure 2:
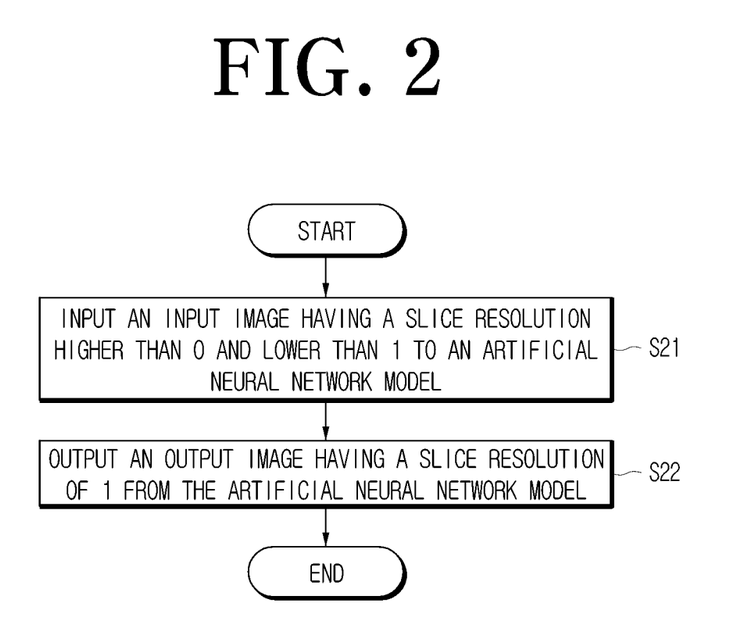
FIG. 2 is a flowchart showing the sequence of a magnetic resonance image processing method performed using a magnetic resonance image processing apparatus according to an embodiment of the present invention.

FIG. 2 is a flowchart showing the sequence of a magnetic resonance image processing method performed using a magnetic resonance image processing apparatus according to an embodiment of the present invention.

Referring to FIG. 2, in the magnetic resonance image processing method performed by the magnetic resonance image processing apparatus 100 according to an embodiment of the present invention, step S210 of inputting an input image having a slice resolution higher than 0 and lower than 1 to the artificial neural network model 400 may be performed.

The input image is a magnetic resonance image, and may include at least one of a k-space image and a DICOM image. A k-space may refer to a temporary image space (typically a matrix) in which the data of a digitized magnetic resonance signal is stored. When the k-space is full (at the end of an MRI scan), data may be mathematically processed, so that a final image is generated. The k-space may hold raw data before the reconstruction of an image. The k-space image may be an image of raw data.

Digital Imaging and Communications in Medicine (DICOM) refers to a medical digital image and communication standard, and is a generic term for various standards used for digital image expressions and communications in medical equipment.

DICOM data may mainly include patient information and media characteristics. For example, various types of medical information data included in the DICOM data are patient-related text information and raw media information collected in a medical field, and the format thereof is not particularly limited. More specifically, the DICOM data may include the biometric information of a patient, medical image information, i.e., a still image of a patient or treatment site generated in a medical field, and medical moving image or video information captured in a medical field. A DICOM image may be a medical image included in the DICOM data.

Furthermore, a magnetic resonance image may be a 3D image formed by accumulating a plurality of image slices. Furthermore, a plurality of image slices may be generated by slicing the 3D medical image in each direction.

Figure 3:
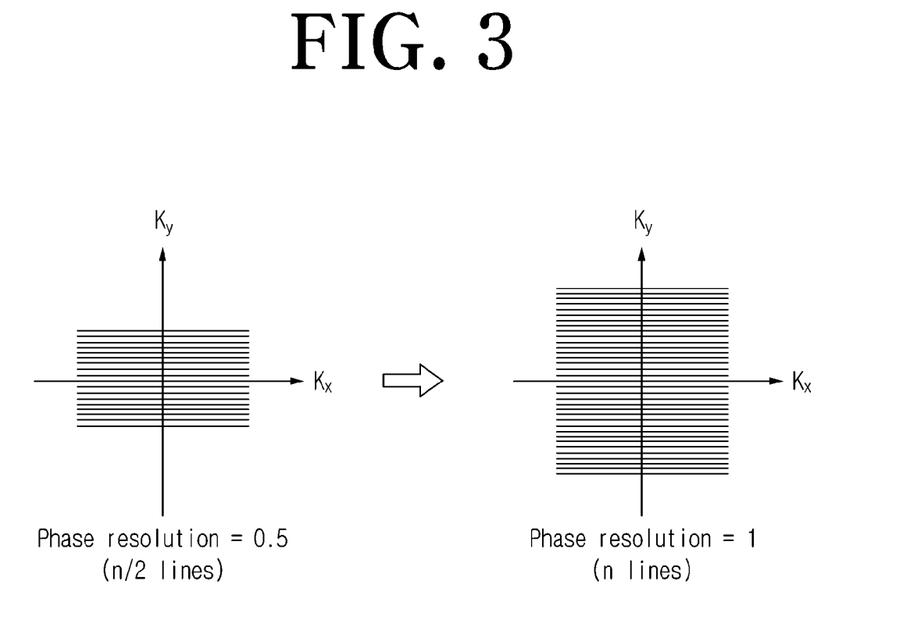
FIG. 3 is a diagram illustrating the differences between full sampling and sub-sampling according to an embodiment of the present invention.
Figure 4:
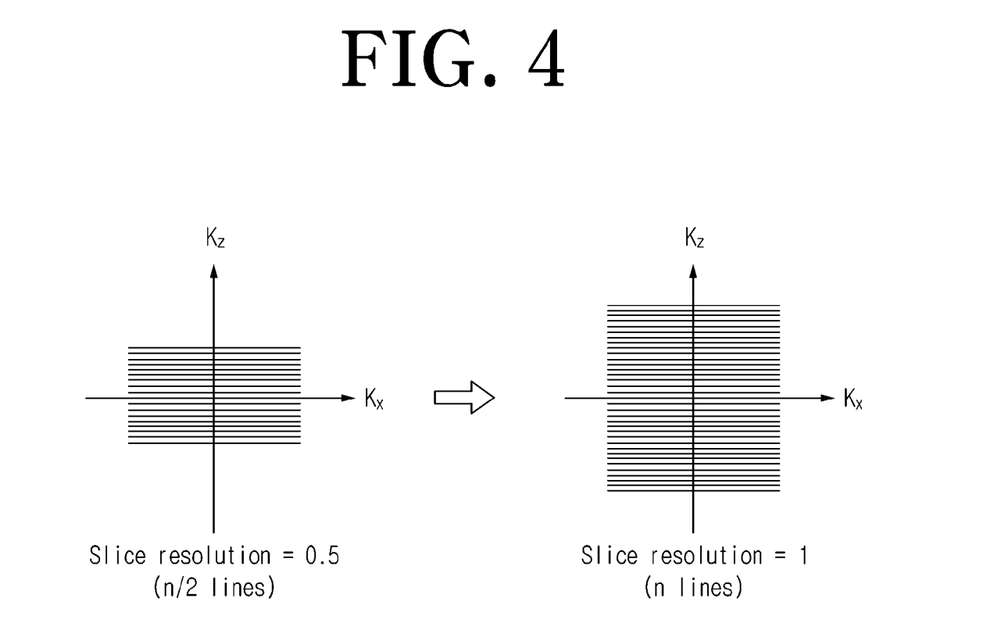
FIG. 4 is a diagram illustrating slice resolutions according to an embodiment of the present invention.

FIG. 3 is a diagram illustrating the differences between full sampling and sub-sampling according to an embodiment of the present invention. FIG. 4 is a diagram illustrating slice resolutions according to an embodiment of the present invention.

Referring to FIGS. 3 and 4, a magnetic resonance image may include at least any one of acceleratedly imaged k-space data and DICOM data generated based on acceleratedly imaged k-space data.

Accelerated imaging may refer to acquiring an image having a low resolution by acquiring a signal in a narrower range in a phase encoding direction in a k-space. Furthermore, accelerated imaging may refer to acquiring a sub-sampled magnetic resonance signal by shortening MRI imaging time when medical image data is an MRI-imaged image. The sub-sampled magnetic resonance signal may be a magnetic resonance signal sampled at a sampling rate lower than the Nyquist sampling rate. In other words, an acceleratedly imaged magnetic resonance image may be an image acquired by sampling a magnetic resonance signal at a sampling rate lower than the Nyquist sampling rate. A sub-sampled magnetic resonance image may be an image including artifacts, which are various artificial images.

For example, the number of lines of a fully sampled magnetic resonance signal may be n, and the number of lines of a sub-sampled magnetic resonance signal may be n/2. In this case, when the degree of reduction in the number of sampling lines is a multiple of ½, the acceleration factor of magnetic resonance imaging may be considered to be 2. When the degree of reduction in the number of sampling lines is a multiple of ⅓ or a multiple of ¼, the acceleration factor may be considered to be 3 or 4.

A phase resolution may be a resolution that is measured based on a phase encoding direction Ky, which is a direction in which lines sampled in the process of sampling a magnetic resonance signal are stacked. In this case, the value of a phase resolution may refer to the relative size of the phase encoding axis data range of actually acceleratedly imaged k-space data when the phase encoding axis data range of the fully sampled k-space data is set to 1. Furthermore, a readout resolution may be a resolution that is measured based on a direction Kx in which sampled lines extend. The value of a readout resolution may refer to the relative size of a readout direction data range in k-space like the value of a phase resolution. Moreover, a slice resolution may be a resolution that is measured based on a slice stack direction Kz that is orthogonal to the axial direction Kz of a coil or to the phase encoding direction Ky and the readout direction Kx. The value of a slice resolution may refer to the relative size of a data range in a slice stack direction in k-space.

The input image may include an image in which at least one of a phase resolution and a readout resolution is 1. The input image may include an image in which a slice resolution is higher than 0 and lower than 1.

Figure 5:
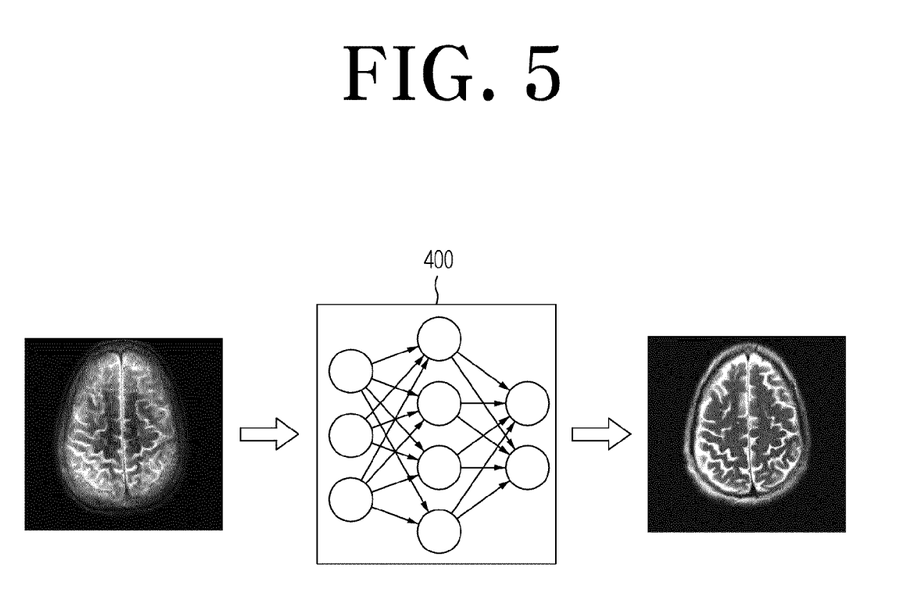
FIG. 5 is a diagram showing the input and output of an artificial neural network model according to an embodiment of the present invention.

FIG. 5 is a diagram showing the input and output of an artificial neural network model according to an embodiment of the present invention.

Referring to FIG. 5, the artificial neural network model 400 may be a set of algorithms for learning the correlation between at least one sub-sampled magnetic resonance image and at least one fully sampled magnetic resonance image by using statistical machine learning results. The artificial neural network model 400 may include at least one neural network. The neural network may include network models such as a Deep Neural Network (DNN), a Recurrent Neural Network (RNN), a Bidirectional Recurrent Deep Neural Network (BRDNN), a Multilayer Perceptron (MLP) network, and a Convolutional Neural Network (CNN), but is not limited thereto.

For example, the artificial neural network model 400 may be a model constructed by learning the correlation between at least one sub-sampled magnetic resonance image and at least one fully sampled magnetic resonance image using a neural network on the basis of every pixels of at least one sampling line stacked along a phase encoding direction. Furthermore, the artificial neural network model 400 may be constructed using various types of additional data other than a sub-sampled magnetic resonance image and a fully sampled magnetic resonance image. For example, at least one of k-space data, real image data, imaginary image data, magnitude image data, phase image data, sensitivity data of a multi-channel RF coil, and noise pattern image data corresponding to a magnetic resonance image may be used as the additional data.

Figure 6:
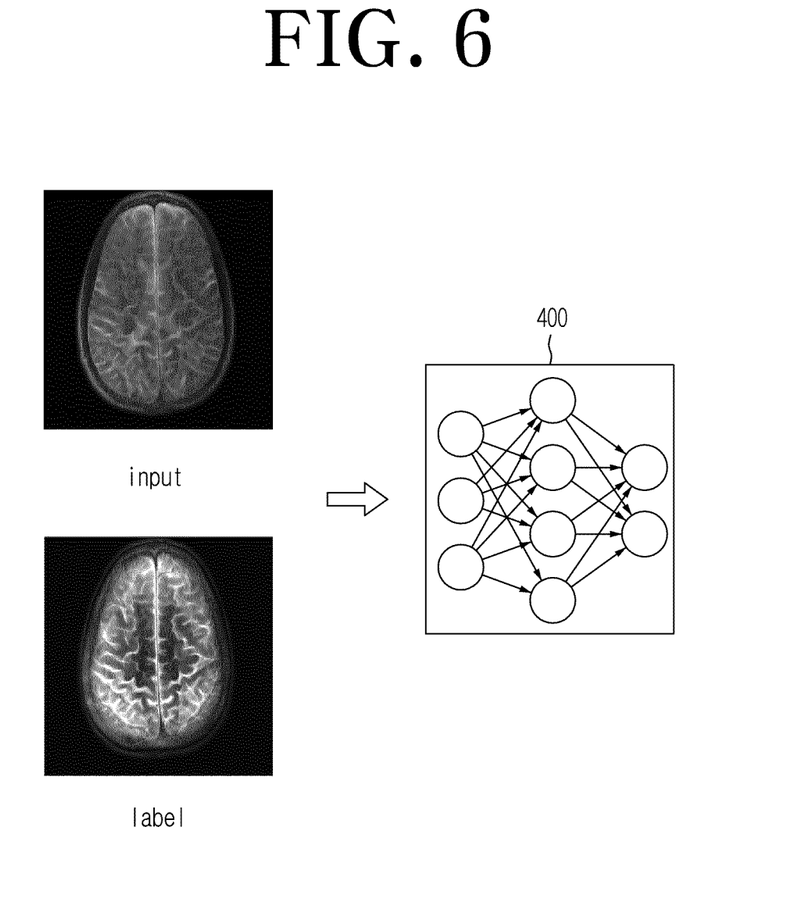
FIG. 6 is a diagram showing the training of an artificial neural network model according to an embodiment of the present invention.

FIG. 6 is a diagram showing the training of an artificial neural network model according to an embodiment of the present invention.

Referring to FIG. 6, the artificial neural network model 400 may have been trained with image data having a slice resolution higher than 0 and lower than 1 set as training input data and image data having a slice resolution of approximately 1 set as training label data.

The training input data may include image data in which the slice resolution thereof, which is measured based on the setting of the slice resolution of an input image to 1, is higher than 0 and lower than 1.

For example, when the slice resolution of an input image is 0.5, training input data may have a slice resolution higher than 0% of 0.5 and lower than 100% of 0.5.

More specifically, the slice resolution of the training input data may be 0.25, which is 50% of 0.5, which is the slice resolution of the input image. In other words, the slice resolution of the training input data may have a value obtained by multiplying the slice resolution of the input image by a magnification corresponding to the slice resolution of the input image. The slice resolution of the training input data for the slice resolution of the input image may be the same as the slice resolution of the input image.

The training input data may include a training image and a slice image adjacent to the training image. For example, the training input data may include a training image and a slice image adjacent to the training image, and the artificial neural network model may receive and be trained on a combination of the training image and the slice image adjacent to the training image. In other words, when an image having a low slice resolution is reconstructed, the data of a corresponding image slice and another image slice adjacent thereto may be used.

Meanwhile, in this case, the combination of images may refer to forming a plurality of slice images into one input set or superimposing a plurality of slice images on the same plane. However, other methods may be applied as long as they correspond to a method capable of simultaneously inputting a plurality of slice images to the artificial neural network model.

The training label data may include image data having a slice resolution equal to or smaller than the slice resolution of the input image. For example, when the slice resolution of the input image is 0.5, the training label data may include image data having a slice resolution of 0.5.

In order to correspond to the training input data, the input image of the artificial neural network model 400 may include a target image whose slice resolution is to be increased and a slice image adjacent to the target image. A combination of the target image and the slice image adjacent to the target image may be input to the artificial neural network model 400. Accordingly, the quality of an output image output from the artificial neural network model 400 may be improved by performing image reconstruction using input image data optimized for the training input data on which the artificial neural network model 400 is trained.

Furthermore, the artificial neural network model 400 may have been trained with image data having a readout resolution lower than 1 set as an input and image data having a readout resolution of 1 set as a label. Furthermore, the artificial neural network model 400 may have been trained with image data having a phase resolution lower than 1 set as an input and image data having a phase resolution of 1 set as a label.

Thereafter, step S220 of outputting an output image having a slice resolution of 1 from the artificial neural network model 400 may be performed.

Accordingly, when a low-resolution magnetic resonance image having a slice resolution higher than 0 and lower than 1 is input to the artificial neural network model 400, reconstruction is performed, and thus an improved magnetic resonance image having a slice resolution of 1 can be output.

The above-described magnetic resonance image processing apparatus 100 and magnetic resonance image processing method according to the embodiments of the present invention may acquire a magnetic resonance image having a slice resolution of 1 by using an acceleratedly imaged magnetic resonance image having a slice resolution higher than 0 and lower than 1 and the artificial neural network model 400.

Furthermore, the magnetic resonance image processing apparatus 100 and magnetic resonance image processing method according to the embodiments of the present invention may acquire a magnetic resonance image having an improved slice resolution and an improved resolution by using the artificial neural network model 400 trained only on training image data having a low slice resolution when there is no training image data having a high slice resolution.

Meanwhile, the magnetic resonance image processing method according to the embodiment of the present invention may be implemented in the form of a storage medium including instructions executable by a computer, such as a program module executed by a computer. Computer-readable media may be any available media that can be accessed by a computer, and include both volatile and nonvolatile media and removable and non-removable media. Furthermore, the computer-readable media may include computer storage media. The computer storage media include both volatile and nonvolatile media and removable and non-removable media implemented using any method or technology for the storage of information such as computer-readable instructions, data structures, program modules or other data. Although the method and system of the present invention have been described in connection with the specific embodiments, some or all of their components or steps may be implemented using a computer system having a general-purpose hardware architecture.

The above description is merely illustrative of the technical spirit of the present invention, and those of ordinary skill in the art to which the present invention pertains may make various modifications and alterations without departing from the essential features of the present invention. Accordingly, the embodiments disclosed in the present invention are not intended to limit the technical spirit of the present invention but are intended to describe the technical spirit of the present invention, and the scope of the technical spirit of the present invention is not limited by these embodiments. The scope of protection of the present invention should be interpreted by the following claims, and all technical spirits falling within the scope equivalent thereto should be interpreted as being included in the scope of the present invention.

What is claimed is:

1. A magnetic resonance image processing method, the magnetic resonance image processing method being performed by a magnetic resonance image processing apparatus, the magnetic resonance image processing method comprising:
   inputting an input image obtained by accelerated imaging, having a slice resolution higher than 0% and lower than 100% to an artificial neural network model; and
   outputting an output image having a slice resolution of 100% from the artificial neural network model, and
   wherein the input image includes a target image for which a slice resolution is to be increased and a slice image adjacent to the target image,
   wherein inputting the input image to the artificial neural network model comprises inputting a combination of the target image and the slice image adjacent to the target image to the artificial neural network model, and
   wherein the slice resolution is defined as a relative size of k-space data range measured in the slice stack direction (Kz) in k-space, corresponding to the input image obtained through accelerated MRI scanning.

2. The magnetic resonance image processing method of claim 1, wherein the artificial neural network model has been trained with training input data including image data having a slice resolution higher than 0% and lower than 100% and training label data including image data having a slice resolution of 100%.

3. The magnetic resonance image processing method of claim 2, wherein:
   the training input data includes image data having a slice resolution higher than 0% and lower than 100% that is measured based on a setting of a slice resolution of the input image to 100%; and
   the training label data includes image data having a same slice resolution as the input image.

4. The magnetic resonance image processing method of claim 2, wherein:
   the training input data includes a training image and a slice image adjacent to the training image; and
   a combination of the training image and the slice image adjacent to the training image is input to the artificial neural network model, and the artificial neural network model is trained on the combination.

5. The magnetic resonance image processing method of claim 1, wherein the input image includes at least one of a k-space image and a DICOM image.

6. A magnetic resonance image processing apparatus, configured to input an input image obtained by accelerated imaging, having a slice resolution higher than 0% and lower than 100% to an artificial neural network model, and obtain an output image having a slice resolution of 100% from the artificial neural network model, and
   wherein the input image includes a target image for which a slice resolution is to be increased and a slice image adjacent to the target image,
   wherein the magnetic resonance image processing apparatus is configured to input a combination of the target image and the slice image adjacent to the target image to the artificial neural network model, and
   wherein the slice resolution is defined as a relative size of k-space data range measured in the slice stack direction (Kz) in k-space, corresponding to the input image obtained through accelerated MRI scanning.

7. The magnetic resonance image processing apparatus of claim 6, wherein the artificial neural network model has been trained with training input data including image data having a slice resolution higher than 0% and lower than 100% and training label data including image data having a slice resolution of 100%.

8. The magnetic resonance image processing apparatus of claim 7, wherein:
the training input data includes image data having a slice resolution higher than 0% and lower than 100% that is measured based on a setting of a slice resolution of the input image to 100%; and
the training label data includes image data having a same slice resolution as the input image.

9. The magnetic resonance image processing apparatus of claim 7, wherein:
the training input data includes a training image and a slice image adjacent to the training image; and
a combination of the training image and the slice image adjacent to the training image is input to the artificial neural network model, and the artificial neural network model is trained on the combination.

10. The magnetic resonance image processing apparatus of claim 6, wherein the input image includes at least one of a k-space image and a DICOM image.

* * * * *